United States Patent
Drews

(10) Patent No.: US 10,591,503 B2
(45) Date of Patent: Mar. 17, 2020

(54) FLOW CELL LIQUID DEGASSING SYSTEM AND METHOD

(71) Applicant: Illumina, Inc., San Diego, CA (US)

(72) Inventor: Bradley Kent Drews, Poway, CA (US)

(73) Assignee: ILLUMINA, INC., San Diego, CA (US)

( * ) Notice: Subject to any disclaimer, the term of this patent is extended or adjusted under 35 U.S.C. 154(b) by 266 days.

(21) Appl. No.: 15/841,076

(22) Filed: Dec. 13, 2017

(65) Prior Publication Data
US 2018/0188281 A1    Jul. 5, 2018

Related U.S. Application Data

(60) Provisional application No. 62/442,749, filed on Jan. 5, 2017.

(30) Foreign Application Priority Data

Mar. 24, 2017    (GB) .................................. 1704768.9

(51) Int. Cl.
*G01N 21/05*    (2006.01)
*G01N 21/11*    (2006.01)
(Continued)

(52) U.S. Cl.
CPC ......... *G01N 35/1097* (2013.01); *G01N 21/05* (2013.01); *G01N 21/11* (2013.01);
(Continued)

(58) Field of Classification Search
CPC ... G01N 2021/0162; G01N 2021/0325; G01N 2021/115; G01N 2021/6439; G01N 2035/00237; G01N 2035/1034; G01N 21/05; G01N 21/11; G01N 35/00069; G01N 35/1004; G01N 35/1095; G01N 35/1097
See application file for complete search history.

(56) References Cited

U.S. PATENT DOCUMENTS

2009/0249949 A1* 10/2009 Kepler ............... B01D 19/0031
                                                                  95/44
2010/0111768 A1    5/2010 Banerjee et al.
(Continued)

FOREIGN PATENT DOCUMENTS

CN    203178290    3/2013

OTHER PUBLICATIONS

GB Search Report, dated Sep. 26, 2017, in Application No. GB1704768.9.
(Continued)

*Primary Examiner* — Jennifer Wecker
(74) *Attorney, Agent, or Firm* — Illumina, Inc.

(57) ABSTRACT

A system utilizes a flow cell for holding an analyte of interest for examination, such as a genetic material to be imaged for sequencing. Liquids, such as reagents and washing fluids are introduced into the flow cell during operations. A degasser removes gasses from at least some of the liquids before introduction into the flow cell. The liquids may be resident in the flow cell during detection operations, such as imaging. At least one fluid may be moved bidirectionally into and from the flow cell, such as for reuse. Another fluid may be moved unidirectionally through the flow cell to remove bubbles that may be present in the system.

20 Claims, 6 Drawing Sheets

(51) Int. Cl.
  *G01N 35/10*   (2006.01)
  *G01N 35/00*   (2006.01)
  *G01N 21/03*   (2006.01)
  *G01N 21/01*   (2006.01)
  *G01N 21/64*   (2006.01)

(52) U.S. Cl.
  CPC ... *G01N 35/00069* (2013.01); *G01N 35/1004* (2013.01); *G01N 35/1095* (2013.01); *G01N 2021/0162* (2013.01); *G01N 2021/0325* (2013.01); *G01N 2021/115* (2013.01); *G01N 2021/6439* (2013.01); *G01N 2035/00237* (2013.01); *G01N 2035/1034* (2013.01)

(56) References Cited

U.S. PATENT DOCUMENTS

| | | |
|---|---|---|
| 2012/0004143 A2 | 1/2012 | Belgrader et al. |
| 2012/0154818 A1 | 6/2012 | Kim et al. |
| 2013/0260372 A1 | 10/2013 | Buermann et al. |
| 2014/0080205 A1* | 3/2014 | Posner .................... F04B 19/00 435/287.3 |

OTHER PUBLICATIONS

PCT/US2017/067843, International Search Report and Written Opinion dated Apr. 16, 2018, 18 pages.

* cited by examiner

FLOW CELL LIQUID DEGASSING SYSTEM AND METHOD

CROSS-REFERENCE TO RELATED APPLICATIONS

This application claims benefit of priority under to British (GB) Patent Application No. 1704768.9, filed Mar. 24, 2017, which claims benefit of priority to U.S. Patent Application No. 62/442,749, filed Jan. 5, 2017, as well as benefit of priority under 35 U.S.C. § 119(e) to U.S. Patent Application No. 62/442,749, filed Jan. 5, 2017, both of which are hereby incorporated by reference herein in their entireties.

BACKGROUND

Instruments have been developed and continue to evolve for sequencing molecules of interest, particularly DNA, RNA and other biological samples. In advance of sequencing operations, samples of the molecules of interest are prepared in order to form a library or template which will be mixed with reagents and ultimately introduced into a flow cell where individual molecules will attach at sites and be amplified to enhance detectability. In sequencing operations, then, repeating cycles of steps bind the molecules at the sites, tag the bound components, image the components at the sites, and process the resulting image data. Many other applications utilize flow cells for imaging and other forms of analyte detection.

In such systems, fluidic systems (or subsystems) provide the flow of substances (e.g., the reagents) under the control of a control system, such as a programmed computer and appropriate interfaces.

SUMMARY

Details of one or more implementations of the subject matter described in this specification are set forth in the accompanying drawings and the description below. Other features, aspects, and advantages will become apparent from the description, the drawings, and the claims.

In some implementations, a system is provided that may include: flow paths to fluidically connect with a flow cell to support an analyte of interest; a selector valve fluidically coupled to the flow paths, the selector valve to select a liquid recipient from a plurality of liquid recipients and to receive a liquid from the selected liquid recipient to introduce into the flow paths; a pump to be fluidically coupled to the flow cell; a degassing system to degas the selected liquid prior to introduction or re-introduction of the selected liquid into the flow cell; and control circuitry operatively coupled to the selector valve and the pump, the control circuitry having one or more processors and a memory to store machine-executable instructions which, when executed by the one or more processors, control the selector valve to select the selected liquid recipient and control the pump to aspirate the selected liquid from the selected liquid recipient into the flow cell.

In some implementations of the system, the memory may be to store, or may store, further machine-executable instructions which, when executed by the one or more processors, further control the one or more processors to cause the selected liquid to remain in the flow cell during an imaging operation on the analyte in the flow cell.

In some implementations of the system, the memory may be to store, or may store, further machine-executable instructions which, when executed by the one or more processors, further control the one or more processors to cause the selected liquid to be returned to the selected recipient after the selected liquid is introduced into the flow cell.

In some implementations of the system, the degassing system may be fluidically interposed between the selected liquid recipient and the selector valve and the degassing system may be to additionally degas a second liquid selected received by the selector valve from a second liquid recipient selected by the selector valve for introduction into the flow cell.

In some implementations of the system, the memory may be to store, or may store, further machine-executable instructions which, when executed by the one or more processors, further control the one or more processors to cause the second liquid to be directed through the flow cell and into a disposal recipient.

In some implementations of the system, the second liquid may include a wash liquid to wash the flow cell.

In some implementations of the system, the degassing system may be fluidically interposed between the selected liquid recipient and the selector valve.

In some implementations, a system may be provided that includes flow paths to fluidically connect with a flow cell to support an analyte of interest; an imaging system to image the analyte supported in the flow cell; a selector valve fluidically coupled to the flow paths, the selector valve to select between liquid recipients of a plurality of liquid recipients containing respective liquids and to select first and second liquids of the liquids from the respective liquid recipients to introduce into the flow cell; a pump to be fluidically coupled to the flow cell to draw the selected first and second liquids from the respective recipients into the flow cell; a degassing system to degas the selected first and second liquids prior to introduction into the flow cell; and control circuitry operatively coupled to the one or more selector valves and the pump, the control circuitry having one or more processors and a memory to store, or storing, machine-executable instructions which, when executed by the one or more processors, control the selector valve to separately select the liquid recipients for the first liquid and the second liquid and control pump to draw the first liquid and the second liquid from the respective liquid recipients into the flow cell.

In some implementations of the system, the memory may be to store, or may store, further machine-executable instructions which, when executed by the one or more processors, further control the one or more processors to cause the first liquid to remain in the flow cell during an imaging operation on the analytes in the flow cell.

In some implementations of the system, the memory may be to store, or may store, further machine-executable instructions which, when executed by the one or more processors, further control the one or more processors to cause the first liquid to be returned to the respective recipient after being flowed into the flow cell.

In some implementations of the system, the memory may be to store, or may store, further machine-executable instructions which, when executed by the one or more processors, further control the one or more processors to cause the second liquid to flow through the flow cell and into a disposal recipient.

In some implementations of the system, the second liquid may include a wash liquid to wash the flow cell.

In some implementations of the system, the degassing system may be fluidically interposed between the respective liquid recipients and the selector valve.

In some implementations, a method may be provided that includes: selecting a liquid recipient from a plurality of liquid recipients, the selected liquid recipient containing a liquid for introduction into a flow cell containing an analyte of interest; aspirating the liquid from the selected liquid recipient and into the flow cell; and degassing the aspirated liquid before the aspirated liquid is introduced into the flow cell.

In some implementations of the method, the method may further include causing the aspirated liquid to remain resident in the flow cell during an imaging operation on the analyte contained in the flow cell.

In some implementations of the method, the method may further include returning the liquid to the selected liquid recipient after introduction of the liquid into the flow cell.

In some implementations of the method, the method may further include selecting a second liquid recipient containing a second liquid for introduction into the flow cell, causing the second liquid to be aspirated from the second liquid recipient and into the flow cell, and degassing the aspirated second liquid before introduction into the flow cell.

In some implementations of the method, the method may further include bidirectionally flowing the first liquid through the flow cell and unidirectionally flowing the second liquid through the flow cell.

In some implementations of the method, the method may further include disposing of the second liquid following introduction into the flow cell.

In some implementations of the method, the method may further include using a selector valve to select the selected liquid recipient, and the degassing may be performed at a location between the selected liquid recipient and the selector valve.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
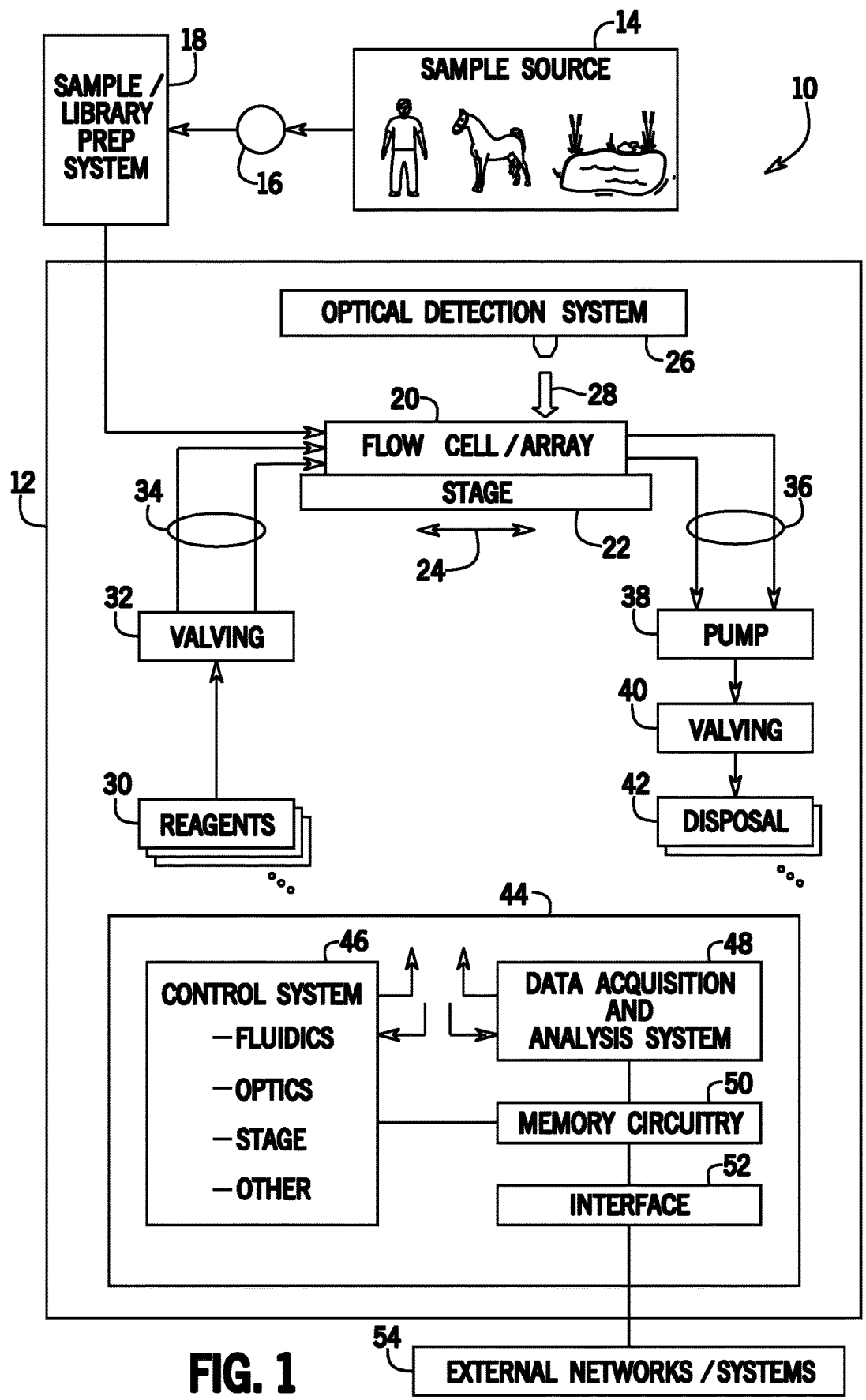
FIG. 1 is a diagrammatical overview of an example sequencing system in which the disclosed techniques may be employed.

FIG. 1 illustrates an implementation of a system 10 configured to process samples of analytes of interest by detecting them in a flow cell. In the illustrated implementation, the system 10 may allow for sequencing of molecules, for example, to determine their components, the component ordering, and generally the structure of the sample. However, the techniques disclosed herein may be applied to any system making use of flow cells for detection of analytes of interest, and into which liquids are introduced during preparation, reaction, detection, or any other process on the flow cell.

In the illustrated implementation, the system 10 includes an instrument 12 that receives and processes a biological sample. A sample source 14 provides the sample 16 which in many cases will include a tissue sample. The sample source may include, for example, an individual or subject, such as a human, animal, microorganism, plant, or other donor (including environmental samples), or any other subject that includes organic molecules of interest, the sequence of which is to be determined. The system may be used with samples other than those taken from organisms, including synthesized molecules. In many cases, the molecules will include DNA, RNA, or other molecules having base pairs the sequence of which may define genes and variants having particular functions of ultimate interest.

The sample 16 is introduced into a sample/library preparation system 18. This system may isolate, break, and otherwise prepare the sample for analysis. The resulting library includes the molecules of interest in lengths that facilitate the sequencing operation. The resulting library is then provided to the instrument 12 where the sequencing operation is performed. In practice, the library, which may sometimes be referred to as a template, is combined with reagents in an automated or semi-automated process, and then introduced to the flow cell prior to sequencing. As used in this disclosure the terms "automated" and "semi-automated" mean that the operations are performed by system programming or configuration with little or no human interaction once the operations are initiated, or once processes including the operations are initiated.

In the implementation illustrated in FIG. 1, the instrument includes a flow cell or array 20 that receives the sample library. The flow cell includes one or more fluidic channels that allow for sequencing chemistry to occur, including attachment of the molecules of the library, and amplification at locations or sites that can be detected during the sequencing operation. For example, the flow cell/array 20 may include sequencing templates immobilized on one or more surfaces at the locations or sites. A "flow cell" may include a patterned array, such as a microarray, a nanoarray, and so forth. In practice, the locations or sites may be disposed in a regular, repeating pattern, a complex non-repeating pattern, or in a random arrangement on one or more surfaces of a support. To enable the sequencing chemistry to occur, the flow cell also allows for introduction of substances, such as including various reagents, buffers, and other reaction media, that are used for reactions, flushing, and so forth. The substances flow through the flow cell and may contact the molecules of interest at the individual sites.

In the instrument the flow cell 20 is mounted on a movable stage 22 that, in this implementation, may be moved in one or more directions as indicated by reference numeral 24. The flow cell 20 may, for example, be provided in the form of a removable and replaceable cartridge that may interface with ports on the movable stage 22 or other components of the system in order to allow reagents and other fluids to be delivered to or from the flow cell 20. The stage is associated with an optical detection system 26 that can direct radiation or light 28 to the flow cell during sequencing. The optical detection system may employ various methods, such as fluorescence microscopy methods, for detection of the analytes disposed at the sites of the flow cell. By way of a non-limiting example, the optical detection system 26 may employ confocal line scanning to produce progressive pixilated image data that can be analyzed to locate individual sites in the flow cell and to determine the type of nucleotide that was most recently attached or bound to each site. Other suitable imaging techniques may also be employed, such as techniques in which one or more points of radiation are scanned along the sample or techniques employing "step and shoot" imaging approaches. The optical detection system 26 and the stage 22 may cooperate to maintain the flow cell and detection system in a static relationship while obtaining an area image, or, as noted, the flow cell may be scanned in any suitable mode (e.g., point scanning, line scanning, "step-and-shoot" scanning).

While many different technologies may be used for imaging, or more generally for detecting the molecules at the sites, presently contemplated implementations may make use of confocal optical imaging at wavelengths that cause excitation of fluorescent tags. The tags, excited by virtue of their absorption spectrum, return fluorescent signals by virtue of their emission spectrum. The optical detection system 26 is configured to capture such signals, to process pixelated image data at a resolution that allows for analysis of the signal-emitting sites, and to process and store the resulting image data (or data derived from it).

In a sequencing operation, cyclic operations or processes are implemented in an automated or semi-automated fashion in which reactions are promoted, such as with single nucleotides or with oligonucleotides, followed by flushing, imaging and de-blocking in preparation for a subsequent cycle. The sample library, prepared for sequencing and immobilized on the flow cell, may undergo a number of such cycles before all useful information is extracted from the library. The optical detection system may generate image data from scans of the flow cell (and its sites) during each cycle of the sequencing operation by use of electronic detection circuits (e.g., cameras or imaging electronic circuits or chips). The resulting image data may then be analyzed to locate individual sites in the image data, and to analyze and characterize the molecules present at the sites, such as by reference to a specific color or wavelength of light (a characteristic emission spectrum of a particular fluorescent tag) that is detected at a specific location, as indicated by a group or cluster of pixels in the image data at the location. In a DNA or RNA sequencing application, for example, the four common nucleotides may be represented by distinguishable fluorescence emission spectra (wavelengths or wavelength ranges of light). Each emission spectrum, then, may be assigned a value corresponding to that nucleotide. Based upon this analysis, and tracking the cyclical values determined for each site, individual nucleotides and their orders may be determined for each site. These sequences may then be further processed to assemble longer segments including genes, chromosomes, and so forth.

In the illustrated implementation, reagents 30 are drawn or aspirated into the flow cell through valving 32. The valving may access the reagents from recipients or vessels in which they are stored, such as through pipettes or sippers (not shown in FIG. 1). The valving 32 may allow for selection of the reagents based upon a prescribed sequence of operations performed. The valving may further receive commands for directing the reagents through flow paths 34 into the flow cell 20. Exit or effluent flow paths 36 direct the used reagents from the flow cell. In the illustrated implementation, a pump 38 serves to move the reagents through the system. The pump may also serve other useful functions, such as measuring reagents or other fluids through the system, aspirating air or other fluids, and so forth. Additional valving 40 downstream of pump 38 allows for appropriately directing the used reagent to disposal vessels or recipients 42.

The instrument further includes a range of circuitry that aids in commanding the operation of the various system components, monitoring their operation by feedback from sensors, collecting image data, and at least partially processing the image data. In the implementation illustrated in FIG. 1, a control/supervisory system 44 includes a control system 46 and a data acquisition and analysis system 48. Both systems will include one or more processors (e.g., digital processing circuits, such as microprocessors, multi-core processors, FPGA's, or any other suitable processing circuitry) and associated memory circuitry 50 (e.g., solid state memory devices, dynamic memory devices, on and/or off-board memory devices, and so forth) that may store machine-executable instructions for controlling, for example, one or more computers, processors, or other similar logical devices to provide certain functionality. Application-specific or general purpose computers may at least partially make up the control system and the data acquisition and analysis system. The control system may include, for example, circuitry configured (e.g., programmed) to process commands for fluidics, optics, stage control, and any other useful functions of the instrument. The data acquisition and analysis system 48 interfaces with the optical detection system to command movement of the optical detection system or the stage, or both, the emission of light for cyclic detection, receiving and processing of returned signals, and so forth. The instrument may also include various interfaces as indicated at reference 52, such as an operator interface that permits control and monitoring of the instrument, transfer of samples, launching of automated or semi-automated sequencing operations, generation of reports, and so forth. Finally, in the implementation of FIG. 1, external networks or systems 54 maybe coupled to and cooperate with the instrument, for example, for analysis, control, monitoring, servicing, and other operations.

It may be noted that while a single flow cell and fluidics path, and a single optical detection system are illustrated in FIG. 1, in some instruments more than one flow cell and fluidics path may be accommodated. For example, in a presently contemplated implementation, two such arrangements are provided to enhance sequencing and throughput. In practice, any number of flow cells and paths may be provided. These may make use of the same or different reagent receptacles, disposal receptacles, control systems, image analysis systems, and so forth. Where provided, the multiple fluidics systems may be individually controlled or controlled in a coordinated fashion. It is to be understood that the phrase "fluidically connected" may be used herein to describe connections between two or more components that place such components in fluidic communication with one another, much in the same manner that "electrically connected" may be used to describe an electrical connection between two or more components. The phrase "fluidically interposed" may be used, for example, to describe a particular ordering of components. For example, if component B is fluidically interposed between components A and C, then fluid flowing from component A to component C would flow through component B before reaching component C.

Figure 2:
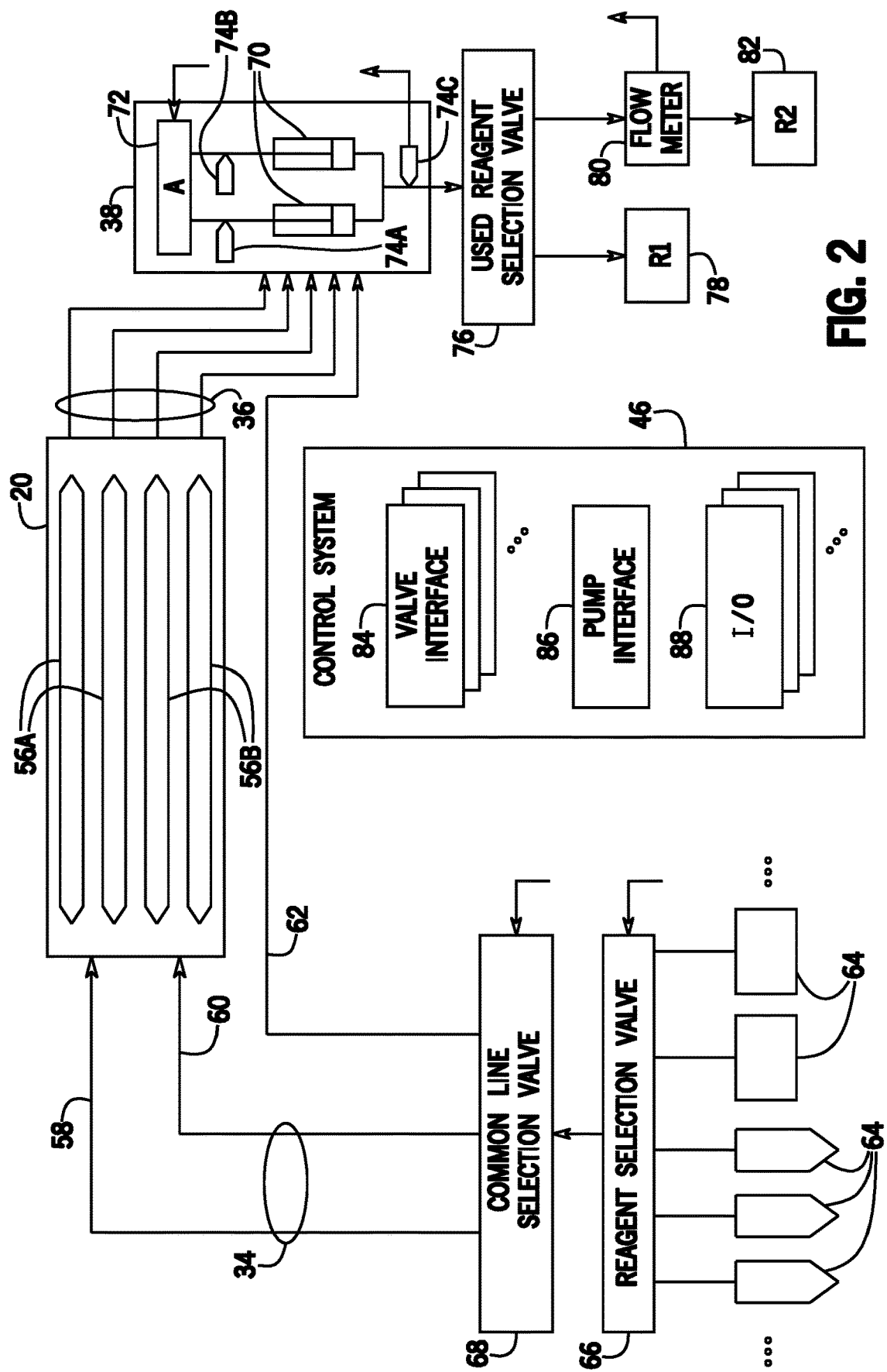
FIG. 2 is a diagrammatical overview of an example fluidic system of the system of FIG. 1.

FIG. 2 illustrates an example fluidic system of the sequencing system of FIG. 1. In the implementation illustrated, the flow cell 20 includes a series of pathways or lanes 56A and 56B which may be grouped in pairs for receiving fluid substances (e.g., reagents, buffers, reaction media) during sequencing operations. The lanes 56A are coupled to a common line 58 (a first common line), while the lanes 56B are coupled to a second common line 60. A bypass line 62 is also provided to allow fluids to bypass the flow cell without entering it. As noted above, a series of vessels or recipients 64 allow for the storage of reagents and other fluids that may be utilized during the sequencing operation. A reagent selector valve 66 is mechanically coupled to a motor or actuator (not shown) to allow selection of one or more of the reagents to be introduced into the flow cell. Selected reagents are then advanced to a common line selector valve 68 which similarly includes a motor (not shown). The common line selector valve may be commanded to select one or more of the common lines 58 and 60, or both common lines, to cause the reagents 64 to flow to the lanes 56A and/or 56B in a controlled fashion, or the bypass line 62 to flow one or more of the reagents through the bypass line.

Used reagents exit the flow cell through lines coupled between the flow cell and the pump 38. In the illustrated implementation, the pump includes a syringe pump having a pair of syringes 70 that are controlled and moved by an actuator 72 to aspirate the reagents and other fluids and to eject the reagents and fluids during different operations of the testing, verification and sequencing cycles. The pump assembly may include various other parts and components, including valving, instrumentation, actuators, and so forth (not shown). In the illustrated implementation, pressure sensors 74A and 74B sense pressure on inlet lines of the pump, while a pressure sensor 74C is provided to sense pressures output by the syringe pump.

Fluids used by the system enter a used reagent selector valve 76 from the pump. This valve allows for selection of one of multiple flow paths for used reagents and other fluids. In the illustrated implementation, a first flow path leads to a first used reagent receptacle 78, while a second flow path leads through a flow meter 80 a second used reagent receptacle 82. Depending upon the reagents used, it may be advantageous to collect the reagents, or certain of the reagents in separate vessels for disposal, and the used reagent selector valve 76 allows for such control.

It should be noted that valving within the pump assembly may allow for various fluids, including reagents, solvents, cleaners, air, and so forth to be aspirated by the pump and injected or circulated through one or more of the common lines, the bypass line, and the flow cell. Moreover, as noted above, in a presently contemplated implementation, two parallel implementations of the fluidics system shown in FIG. 2 are provided under common control. Each of the fluidics systems may be part of a single sequencing instrument, and may carry out functions including sequencing operations on different flow cells and sample libraries in parallel.

The fluidics system operates under the command of control system 46 which implements prescribed protocols for testing, verification, sequencing, and so forth. The prescribed protocols will be established in advance and include a series of events or operations for activities such as aspirating reagents, aspirating air, aspirating other fluids, ejecting such reagents, air and fluids, and so forth. The protocols will allow for coordination of such fluidic operations with other operations of the instrument, such as reactions occurring in the flow cell, imaging of the flow cell and its sites, and so forth. In the illustrated implementation, the control system 46 employs one or more valve interfaces 84 which are configured to provide command signals for the valves, as well as a pump interface 86 configured to command operation of the pump actuator. Various input/output circuits 88 may also be provided for receiving feedback and processing such feedback, such as from the pressure sensors 74A-C and flow meter 80.

Figure 3:
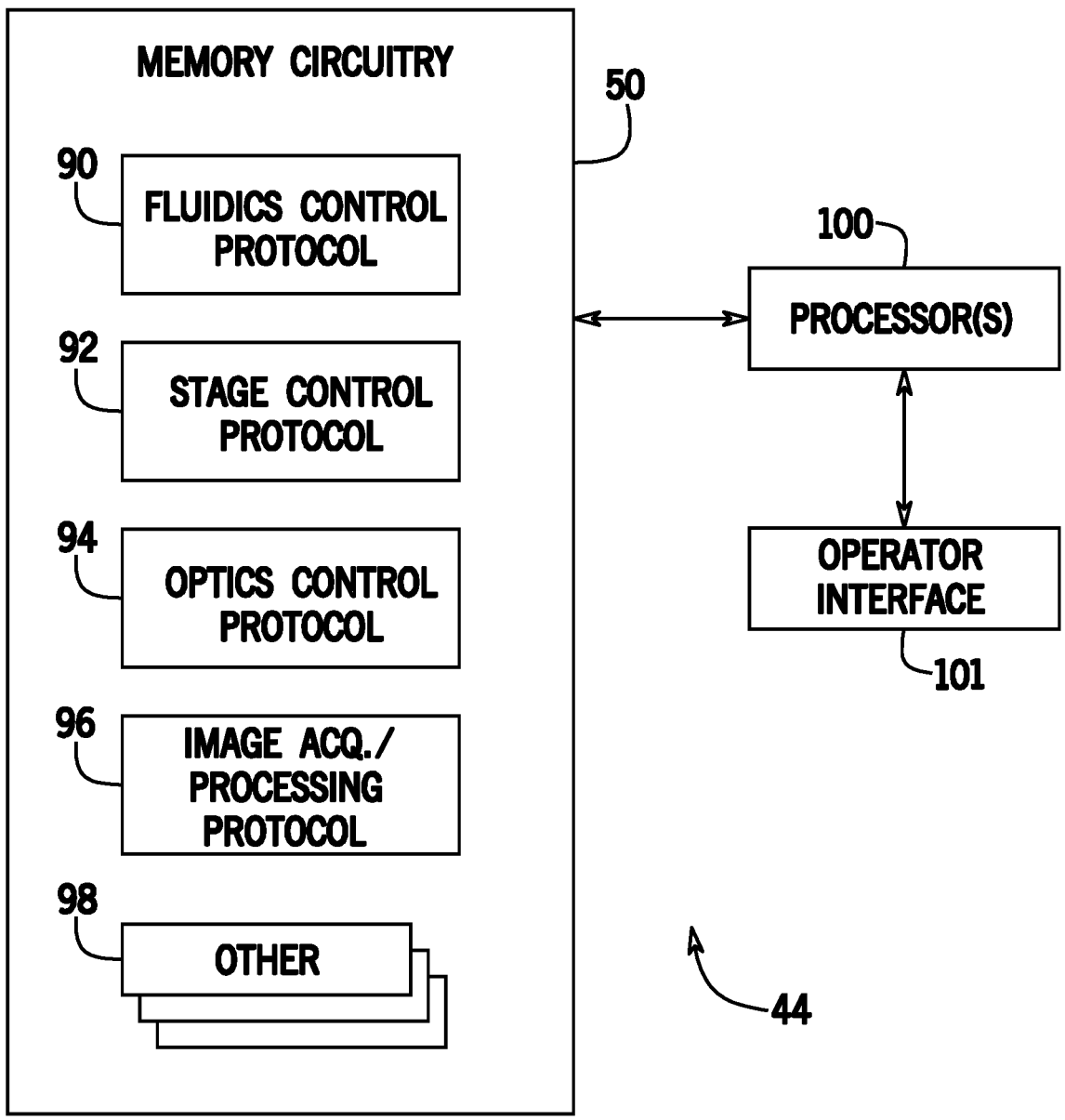
FIG. 3 is a diagrammatical overview of an example processing and control system of the sequencing system of FIG. 1.

FIG. 3 illustrates certain functional components of the control/supervisory system 44. As illustrated, the memory circuitry 50 stores prescribed routines that are executed during testing, commissioning, troubleshooting, servicing, and sequencing operations. Many such protocols and routines may be implemented and stored in the memory circuitry, and these may be updated or altered from time to time. As illustrated in FIG. 3, these may include a fluidics control protocol 90 for controlling the various valves, pumps, and any other fluidics actuators, as well as for receiving and processing feedback from fluidics sensors, such as valves, and flow and pressure sensors. A stage control protocol 92 allows for moving the flow cell as desired, such as during imaging. An optics control protocol 94 allows for commands to be issued to the imaging components to illuminate portions of the flow cell and to receive returned signals for processing. An image acquisition and processing protocol 96 allows for the image data to be at least partially processed for extraction of useful data for sequencing. Other protocols and routines may be provided in the same or different memory circuitry as indicated by reference 98. In practice, the memory circuitry may be provided as one or more memory devices, such as both volatile and non-volatile memories. This memory may be within the instrument, and some may be off-board.

One or more processors 100 access the stored protocols and implement them on the instrument. As noted above, the processing circuitry may be part of application-specific computers, general-purpose computers, or any suitable hardware, firmware and software platform. The processors and the operation of the instrument may be commanded by human operators via an operator interface 101. The operator interface may allow for testing, commissioning, troubleshooting, and servicing, as well as for reporting any issues that may arise in the instrument. The operator interface may also allow for launching and monitoring sequencing operations.

Figure 4:
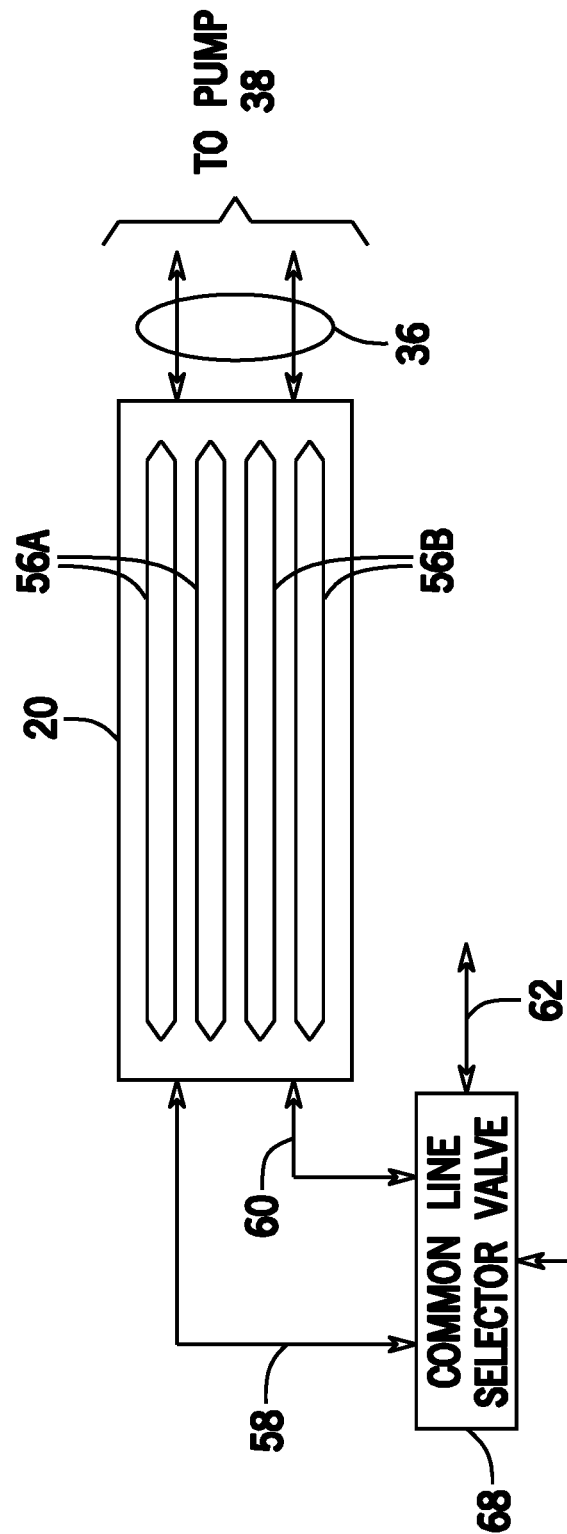
FIG. 4 is a diagrammatical view of an example portion of the fluidic system for providing liquids to a flow cell and for degassing at least some of the liquids.

FIG. 4 illustrates an example implementation of a fluidics system for providing liquids to a flow cell. The flow cell may be any desired type and may be used for any useful application, including for imaging biological samples as discussed above. More generally, however, the fluidics system may be employed in other applications or environments, such as those where a sample is supported in a flow cell and liquids, such as reagents, are pumped into the flow cell (e.g., by aspiration) and detection or analysis operations (e.g., imaging) performed on the sample in the flow cell.

In FIG. 4, the flow cell 20 is illustrated as being coupled downstream of the common line selector valve 68 by flow lines 58 and 60. The common line selector valve is also coupled to the bypass line 62. Downstream of the flow cell, lines 36 couple the flow cell to a pump 38 as described above. The common line selector valve receives reagents and other liquids from the reagent selector valve 66. As noted above, the reagent selector valve is in fluid communication with reagent recipients as indicated by reference numeral 64 and FIG. 4. In the implementation illustrated in FIG. 4, the reagent selector valve 66 is also coupled to recipients 106 and 108, which are among the reagent or other liquid recipients that can be selected and accessed by the reagent selector valve 66 (a reagent or liquid recipient selected by the reagent selector valve 66 may be referred to as a selected liquid recipient, for example). As described above, the pump 38 may aspirate any one of the liquids available to the system through the reagent selector valve 66. Moreover, it should be noted that the liquids may be caused to flow through the flow cell by appropriate positioning of the common line selector valve 68, or the liquids may flow through the bypass line 62. Further, any liquids aspirated by the pump from the various recipients may also be forced back into the recipients if desired, such as for reuse of one or more of the reagents or liquids.

In the implementation of FIG. 4, the reagent selector valve 66 may cause liquids to be aspirated from recipients 106 and 108 through a vacuum degasser 104. Liquid lines 110 and 112 are coupled to the recipients 106 and 108 through the degasser. In the illustrated implementation, the degasser comprises a vacuum pump 114 coupled to a vacuum chamber 116. Semi-permeable, e.g., with a nominal cross-membrane air-flow rate of about 0.74 cc/min at 75 mmHg, tubes 118 and 120 are disposed in the vacuum chamber. When a vacuum is drawn on the chamber, liquid in either of these tubes is degassed by drawing entrained or dissolved gases through the walls of the tubes. Where desired, more than one such vacuum chamber may be provided, and each tube or flow path disposed in a respective vacuum chamber. Similarly, where the vacuum pump is capable of providing sufficient vacuum to more than one chamber, such chambers may be coupled in series, or a separate vacuum pump may be used for each. As described in greater detail below, one or more of the liquids degassed in this manner may be returned to its recipient at least some of the time, as indicated by the double-ended arrow between the reagent selector valve and the recipient 106. Other liquids may not be returned in this manner, as in the case of the liquid aspirated from recipient 108.

In practice, one or more of the reagents or other liquids utilized in preparation for sequencing or during sequencing may be degassed upstream of the flow cell. It should be noted, however, that these techniques may be used in applications other than sequencing or even biological molecule detection. More generally, any system or application utilizing a flow cell for analyte imaging or detection may make use of the degassing techniques described. Further, where more than one liquid is degassed, these may be grouped in a single vacuum chamber 116 as illustrated, or more than one vacuum chamber or vacuum system may be used. In a presently contemplated implementation, as noted above, the fluidics system illustrated has two parallel sides each serving flow cells and comprising pumps, valves, flow paths, and so forth. In such implementations, to separate degassers may be used.

One or more liquids may be degassed to improve performance of the system. In the implementation illustrated, two liquids are degassed, with one being directed bi-directionally into and out of an inlet to the flow cell during use, and the other being passed unidirectionally through the flow cell (in through an inlet and out through a separate outlet) during other periods of use. The liquid in this implementation that is aspirated into the flow cell and returned to its recipient 106 may include a reagent mixture that remains resident in the flow cell during imaging of the analytes and is then returned to its recipient for reuse. From time to time, the re-used reagent may be drawn fully through the flow cell for disposal and replaced with fresh reagent. The liquid that is degassed and that flows unidirectionally through the flow cell, in this implementation, may be a wash liquid which is aspirated during one or more phases of imaging or analysis to flush the flow cell.

Figure 5:
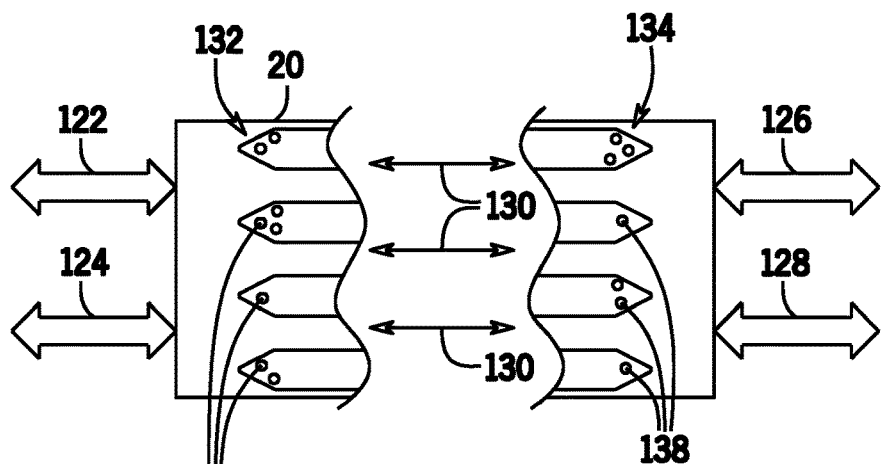
FIG. 5 is a diagrammatical view of an example flow cell illustrating nucleation of bubbles during use.
Figure 6:
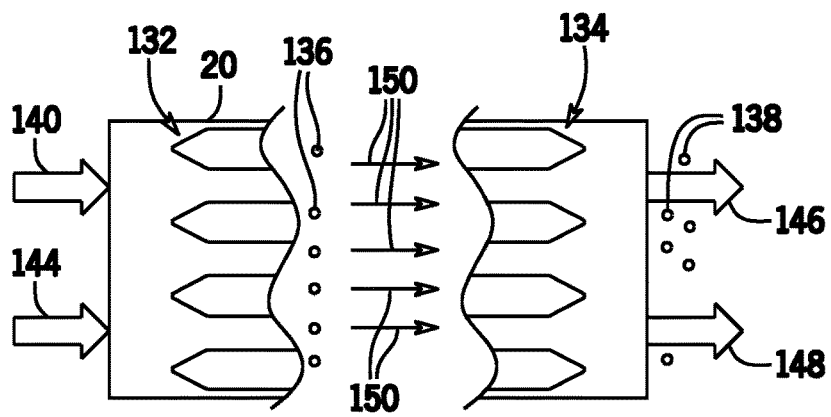
FIG. 6 is a diagrammatical view of an example flow cell illustrating clearing of bubbles from the flow cell.

FIGS. 5 and 6 illustrate the effects of this bi-directional and unidirectional flow. As shown in FIG. 5, when the reagent from recipient 106 flows into or out of the flow cell as indicated by arrows 122 and 124, it may partially exit the flow cell as indicated by arrows 126 and 128 as the pump aspirates the liquid to fully fill the flow cell. Arrows 130 illustrate bi-directional flow through the interior passageways of the flow cell. At any point within the flow cell or at points in the flow lines, and particularly at entrance and exit ends 132 and 134 of the flow cell, bubbles may nucleate or become lodged, as indicated by reference numerals 136 and 138. The bubbles may have an adverse effect on imaging, image processing, or other operations. It has been found that the number and frequency of occurrence of bubbles, such as at the ends of the flow cell and at other locations in the system are reduced by degassing via the degasser 104.

While any nucleated bubbles may in some cases remain within the flow cell or near it, as illustrated in FIG. 6 the technique of flushing a liquid unidirectionally through the flow cell may aid in dislodging and removing bubbles and passing them toward the pump and ultimate disposal. In FIG. 6, unidirectional flow into the flow cell is indicated by arrows 140 and 144, with the exit of the liquid being indicated by arrows 146 and 148. Unidirectional flow through the flow cell passageways is indicated by arrows 150. Because the liquid from recipient 108 passes unidirectionally through the flow cell, bubbles 136 at the entrance end tend to be dislodged and flushed from the flow cell. Other bubbles 138 at the exit end of the flow cell are similarly dislodged and moved downstream. The use of a degassed liquid to flush the flow cell may effectively also flush such bubbles and reduce the occurrence of additional bubbles from the washing liquid.

Figure 7:
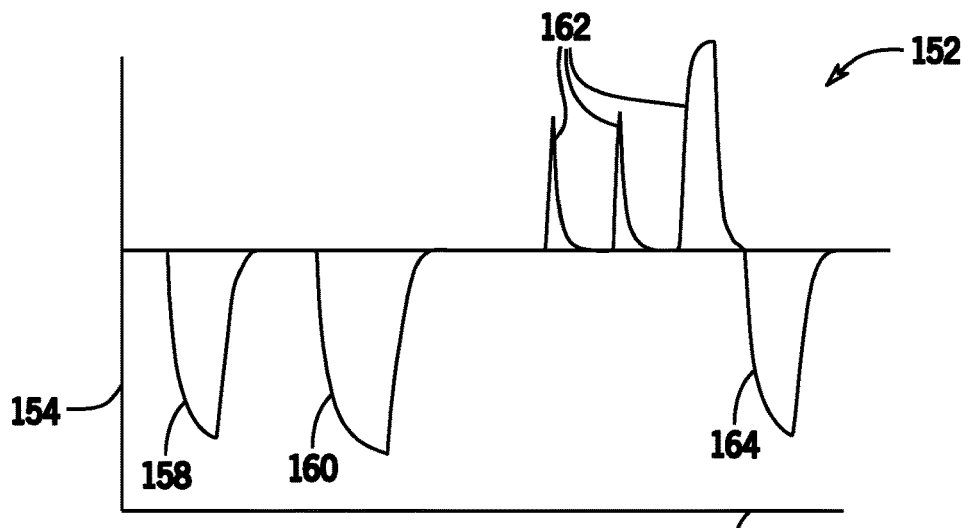
FIG. 7 is a graphical representation of example cycling of pressures in a fluidics system to move liquids into and from a flow cell.
Figure 8:
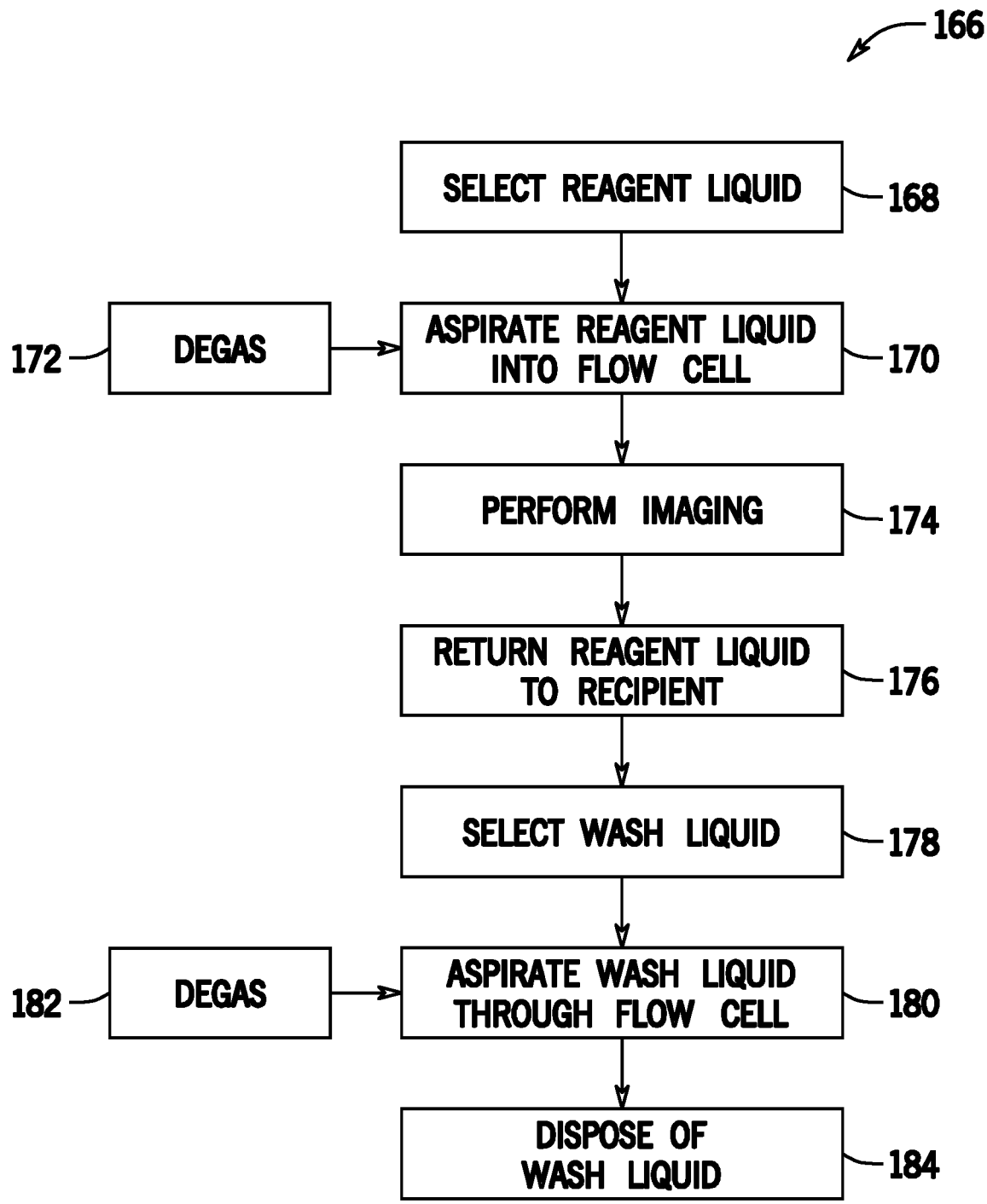
FIG. 8 is a flow chart illustrating example logic for providing liquids to a flow cell and degassing the liquids.

FIG. 7 illustrates an example pressure diagram 152 for aspirating and moving the liquids contained in the recipients 106 and 108 of FIG. 4. FIG. 8 is a flowchart illustrating example logic for this process. In the graphical illustration of FIG. 7, pressure within the flow cell is indicated by vertical axis 154, while time is indicated along horizontal axis 156. In this illustration, pressure events indicated below the center line of axis 154 indicate aspiration by negative pressure, while pressure events above this line indicate ejection or, in this case, return of a reagent to its recipient. The first event 158 shown in FIG. 7 indicates uptake or aspiration of a wash liquid that would be drawn from recipient 108 and passed through the flow cell unidirectionally. This liquid, in this implementation, flushes the flow cell. Following this event, negative pressure event 160 indicates aspiration of the imaging reagent mixture from recipient 106. Following aspiration of this reagent mixture into the flow cell, imaging or detection may be performed as discussed above. The reagent mixture is then returned to recipient 106 by the positive pressure events 162. Following this, the wash liquid may be aspirated again as indicated by the negative pressure event 164.

It should be appreciated that the various negative and positive pressure events illustrated are merely illustrative, and many such events may be performed during analysis, processing, imaging, and other operations on the flow cell. Moreover, these events are accompanied by appropriate shifting of the selector valves to select the liquid to be aspirated from or returned to its recipient under the control of the control circuitry discussed above. Further, other reagents, wash liquids, and liquids and gases with various purposes may be processed by the fluidics system, some of which may be degassed, where desired. Finally, in a presently contemplated implementation, when the processing and analysis are performed in an automated or semi-automated fashion, the degasser described above may be actuated to continuously draw gas from the liquids selected for degassing. Alternatively, the degasser could be cycled at various times during the process to remove or reduce gases from the selected liquids.

This process is illustrated further in the flowchart of FIG. 8. The logic 166 begins at 168 by selecting the reagent or liquid to be aspirated. Again, this selection is performed by appropriately shifting the reagent selector valve described above under the command of the control circuitry and based upon control code stored in memory. Once selected, the reagent liquid is aspirated at 170. The aspiration causes the reagent liquid to traverse the vacuum chamber where it is degassed as indicated at block 172. In the illustrated implementation, this reagent liquid comprises the liquid that is resident in the flow cell during imaging. Accordingly, at 174 in FIG. 8, imaging or detection may be performed by the optics and associated components described above (or any other desired detection equipment). At 176, then, the reagent liquid may be returned to its recipient by a positive pressure event through appropriate commands to the selector valve and pump.

The reagent selector valve may then be shifted to select the wash liquid as indicated at block 178. The liquid may then be aspirated through the flow cell as indicated at 180, with the degasser actuated to degas this liquid as indicated at 182, thereby flushing the flow cell and removing bubbles that may have nucleated. As indicated at 184, then, the wash fluid may be disposed of in an appropriate recipient, as discussed above.

It is believed that multiple advantages may flow from selective degassing as described above. For example, bubbles are removed, flushed, or prevented that can adversely affect imaging, detection, or image processing. Moreover, degassed reagents or liquids may be reused, or reuse may be increased because disposal of the reagents or liquids may be delayed due to the lower levels of entrained or dissolved gas. Further, selective degassing may obtain such benefits to a desired degree without the need to degas all of the reagents or liquids. For example, in some instances it may be cost prohibitive to degas all of the liquids or reagents used, but certain liquids/reagents may be worth degassing. For example, a wash buffer (a liquid used in wash operations) and an imaging buffer (a liquid flowed through the flow cell during imaging operations) may benefit from degassing. Finally, as noted, the selective degassing of at least one liquid that passes bi-directionally through the flow cell, and at least one liquid that passes unidirectionally through the flow cell aids in both reuse and flushing of bubbles and entrained gasses from the lines and flow cell.

The use, if any, of ordinal indicators, e.g., (a), (b), (c) . . . or the like, in this disclosure and claims is to be understood as not conveying any particular order or sequence, except to the extent that such an order or sequence is explicitly indicated. For example, if there are three steps labeled (i), (ii), and (iii), it is to be understood that these steps may be performed in any order (or even concurrently, if not otherwise contraindicated) unless indicated otherwise. For example, if step (ii) involves the handling of an element that is created in step (i), then step (ii) may be viewed as happening at some point after step (i). Similarly, if step (i) involves the handling of an element that is created in step (ii), the reverse is to be understood.

It is also to be understood that the use of "to," e.g., "a valve to switch between two flow paths," may be replaceable with language such as "configured to," e.g., "a valve configured to switch between two flow paths", or the like.

Terms such as "about," "approximately," "substantially," "nominal," or the like, when used in reference to quantities or similar quantifiable properties, are to be understood to be inclusive of values within ±10% of the values specified, unless otherwise indicated.

In addition to the implementations listed in this disclosure, the following additional implementations are to be understood to be within the scope of this disclosure:

Implementation 1: A system including: a flow cell to support an analyte of interest; a selector valve, coupled to the flow cell and to a plurality of liquid recipients containing respective liquids, to select a liquid of a plurality of liquids from a selected recipient to introduce into the flow cell; a pump coupled to the flow cell to aspirate the selected liquid from the selected recipient into the flow cell; and a degassing system to degas the selected liquid prior to introduction into the flow cell.

Implementation 2: The system of implementation 1, in which the selected fluid is allowed to remain in the flow cell during an imaging operation on the analyte in the flow cell.

Implementation 3: The system of implementation 1, in which after introduction into the flow cell the selected liquid is returned to the selected recipient.

Implementation 4: The system of implementation 1, in which the degassing system degasses a second liquid selected by the selector valve to introduce into the flow cell.

Implementation 5: The system of implementation 4, in which after introduction of the second liquid into the flow cell the second liquid is directed to a disposal recipient.

Implementation 6: The system of implementation 5, in which the second liquid includes a wash liquid to wash the flow cell.

Implementation 7: The system of implementation 1, in which the degassing system is disposed between the selected recipient and the selector valve.

Implementation 8: A system including:
a flow cell to support an analyte of interest;
an imaging system to image the analyte supported in the flow cell;
a selector valve, coupled to the flow cell and to a plurality of liquid recipients containing respective liquids, to select first and second liquids of a plurality of liquids from respective recipients to introduce into the flow cell;
a pump coupled to the flow cell to draw the selected first and second liquids from the respective recipients into the flow cell; and
a degassing system to degas the selected first and second liquids prior to introduction into the flow cell.

Implementation 9: The system of implementation 8, in which the first selected liquid is allowed to remain in the flow cell during an imaging operation on the analytes in the flow cell.

Implementation 10: The system of implementation 8, in which after introduction into the flow cell the first selected liquid is returned to the respective recipient.

Implementation 11: The system of implementation 8, in which after introduction of the second selected liquid into the flow cell the second selected liquid is directed to a disposal recipient.

Implementation 12: The system of implementation 11, in which the second selected liquid includes a wash liquid to wash the flow cell.

Implementation 13: The system of implementation 1, in which the degassing system is disposed between the respective recipients and the selector valve.

Implementation 14: A method including:
selecting a liquid from a liquid recipient for introduction into a flow cell containing an analyte of interest;
aspirating the selected liquid from the liquid recipient into the flow cell; and
degassing the selected liquid as it is aspirated from the liquid recipient and before it is introduced into the flow cell.

Implementation 15: The method of implementation 14, including allowing the selected liquid to remain resident in the flow cell during an imaging operation on the analyte.

Implementation 16: The method of implementation 14, including returning the selected liquid to the liquid recipient after introduction into the flow cell.

Implementation 17: The method of implementation 14, including selecting a second liquid for introduction into the flow cell, aspirating the second selected liquid from a second liquid recipient into the flow cell; and degassing the second selected liquid as it is aspirated from the second liquid recipient and before introduction into the flow cell.

Implementation 18: The method of implementation 17, including flowing the first selected liquid bi-directionally through the flow cell, and flowing the second selected liquid uni-directionally through the flow cell.

Implementation 19: The method of implementation 18, including disposing of the second liquid following introduction into the flow cell.

Implementation 20: The method of implementation 14, in which the selected liquid is selected via a selector valve from a plurality of liquids, and in which the selected liquid is degassed between the liquid recipient and the selector valve.

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

What is claimed is:

1. A system comprising:
    flow paths to fluidically connect with a flow cell to support an analyte of interest;
    a selector valve fluidically coupled to the flow paths, the selector valve configured to select a liquid recipient from a plurality of liquid recipients and to receive a liquid from the selected liquid recipient to introduce into the flow paths;
    a pump to be fluidically coupled to the flow cell;
    a degassing system configured to degas the selected liquid prior to introduction or re-introduction of the selected liquid into the flow cell; and
    control circuitry operatively coupled to the selector valve and the pump, the control circuitry having one or more processors and a memory that stores machine-executable instructions which, when executed by the one or more processors, control the one or more processors to cause the selector valve to select the selected liquid recipient and the pump to aspirate the selected liquid from the selected liquid recipient into the flow cell.

2. The system of claim 1, wherein the memory stores further machine-executable instructions which, when executed by the one or more processors, further control the one or more processors to cause the selected liquid to remain in the flow cell during an imaging operation on the analyte in the flow cell.

3. The system of claim 1, wherein the memory stores further machine-executable instructions which, when executed by the one or more processors, further control the one or more processors to cause the selected liquid to be returned to the selected recipient after the selected liquid is introduced into the flow cell.

4. The system of claim 1, wherein the degassing system is fluidically interposed between the selected liquid recipient and the selector valve and the degassing system is configured to additionally degas a second liquid selected received by the selector valve from a second liquid recipient selected by the selector valve for introduction into the flow cell.

5. The system of claim 4, wherein the memory stores further machine-executable instructions which, when executed by the one or more processors, further control the one or more processors to cause the second liquid to be directed through the flow cell and into a disposal recipient.

6. The system of claim 5, wherein the second liquid comprises a wash liquid to wash the flow cell.

7. The system of claim 1, wherein the degassing system is fluidically interposed between the selected liquid recipient and the selector valve.

8. A system comprising:
    flow paths to fluidically connect with a flow cell to support an analyte of interest;
    an imaging system to image the analyte supported in the flow cell;
    a selector valve fluidically coupled to the flow paths, the selector valve configured to select between liquid recipients of a plurality of liquid recipients containing respective liquids and to select first and second liquids of the liquids from the respective liquid recipients to introduce into the flow cell;
    a pump to be fluidically coupled to the flow cell to draw the selected first and second liquids from the respective recipients into the flow cell;
    a degassing system configured to degas the selected first and second liquids prior to introduction into the flow cell; and
    control circuitry operatively coupled to the one or more selector valves and the pump, the control circuitry having one or more processors and a memory that stores machine-executable instructions which, when executed by the one or more processors, control the one or more processors to cause the selector valve to separately select the liquid recipients for the first liquid and the second liquid and the pump to draw the first liquid and the second liquid from the respective liquid recipients into the flow cell.

9. The system of claim 8, wherein the memory stores further machine-executable instructions which, when executed by the one or more processors, further control the one or more processors to cause the first liquid to remain in the flow cell during an imaging operation on the analytes in the flow cell.

10. The system of claim 8, wherein the memory stores further machine-executable instructions which, when executed by the one or more processors, further control the one or more processors to cause the first liquid to be returned to the respective recipient after being flowed into the flow cell.

11. The system of claim 8, wherein the memory stores further machine-executable instructions which, when executed by the one or more processors, further control the one or more processors to cause the second liquid to flow through the flow cell and into a disposal recipient.

12. The system of claim 11, wherein the second liquid comprises a wash liquid to wash the flow cell.

13. The system of claim 1, wherein the degassing system is fluidically interposed between the respective liquid recipients and the selector valve.

14. A method comprising:
    using a selector valve to select a liquid recipient from a plurality of liquid recipients, the selected liquid recipient containing a liquid for introduction into a flow cell containing an analyte of interest;
    aspirating the liquid from the selected liquid recipient and into the flow cell; and
    degassing the aspirated liquid before the aspirated liquid is introduced into the flow cell.

15. The method of claim 14, further comprising causing the aspirated liquid to remain resident in the flow cell during an imaging operation on the analyte contained in the flow cell.

16. The method of claim 14, further comprising returning the liquid to the selected liquid recipient after introduction of the liquid into the flow cell.

17. The method of claim 14, further comprising selecting a second liquid recipient containing a second liquid for introduction into the flow cell, causing the second liquid to be aspirated from the second liquid recipient and into the flow cell, and degassing the aspirated second liquid before introduction into the flow cell.

18. The method of claim 17, further comprising bidirectionally flowing the first liquid through the flow cell and unidirectionally flowing the second liquid through the flow cell.

19. The method of claim 18, further comprising disposing of the second liquid following introduction into the flow cell.

20. The method of claim 14, wherein the degassing is performed at a location between the selected liquid recipient and the selector valve.

\* \* \* \* \*